United States Patent [19]
Holloway

[11] Patent Number: 5,427,650
[45] Date of Patent: Jun. 27, 1995

[54] APPARATUS AND METHOD FOR PREPARATION FOR SEPARATION, RECOVERY, AND RECYCLING OF MUNICIPAL SOLID WASTE AND THE LIKE

[76] Inventor: Clifford C. Holloway, 39368 Camp Dr., Praireville, La. 70769

[21] Appl. No.: 904,217

[22] Filed: Jun. 25, 1992

[51] Int. Cl.⁶ ............................................. D21C 5/02
[52] U.S. Cl. ........................... 162/5; 241/DIG. 38; 162/56
[58] Field of Search ............ 241/16, 38, 24, 23, 241/79.3, 79.1, DIG. 38; 162/4-5, 53, 55, 56, 57, 198, 49, 252, 253, 262, 263, 72, DIG. 3, 238; 210/750, 928, 180; 159/1.1; 203/2; 209/127.1, 214.8, 172.5

[56] References Cited

U.S. PATENT DOCUMENTS

| | | |
|---|---|---|
| 3,070,156 | 12/1962 | Starrett ............................ 162/243 |
| 4,465,591 | 8/1984 | Holz et al. ........................... 162/4 |
| 4,540,467 | 9/1985 | Grube et al. ......................... 162/21 |
| 4,566,942 | 1/1986 | Holz .................................... 162/4 |
| 4,650,125 | 3/1987 | Pellhammer ......................... 162/4 |
| 4,816,117 | 3/1989 | Pfalzer et al. ........................ 162/4 |
| 4,977,943 | 12/1990 | Mizabe ................................. 162/5 |
| 5,122,228 | 6/1992 | Bouchette et al. ..................... 162/5 |

FOREIGN PATENT DOCUMENTS 0768865 10/1980 U.S.S.R. ........................... 162/53

Primary Examiner—Brenda Adele Lamb
Attorney, Agent, or Firm—John C. Garvin, Jr.; Harold W. Hilton

[57] ABSTRACT

Apparatus and method for separation, recovery, and recycling municipal solid waste and the like by introducing solid waste materials into a rotatable pressure vessel, rotating, pressurizing, adding pH controlling chemicals and heating the pressure vessel and thus the waste material while simultaneously applying a mixing action to the solid waste material. The addition of a predetermined amount of pH controlling chemicals and the application of a vacuum serve to control the moisture content of the final fine organic portion of the processed material. Organic contents of the vessel are pulped and sterilized when processed to facilitate ease of separation and prepare the resulting cellulose material for use.

12 Claims, 3 Drawing Sheets

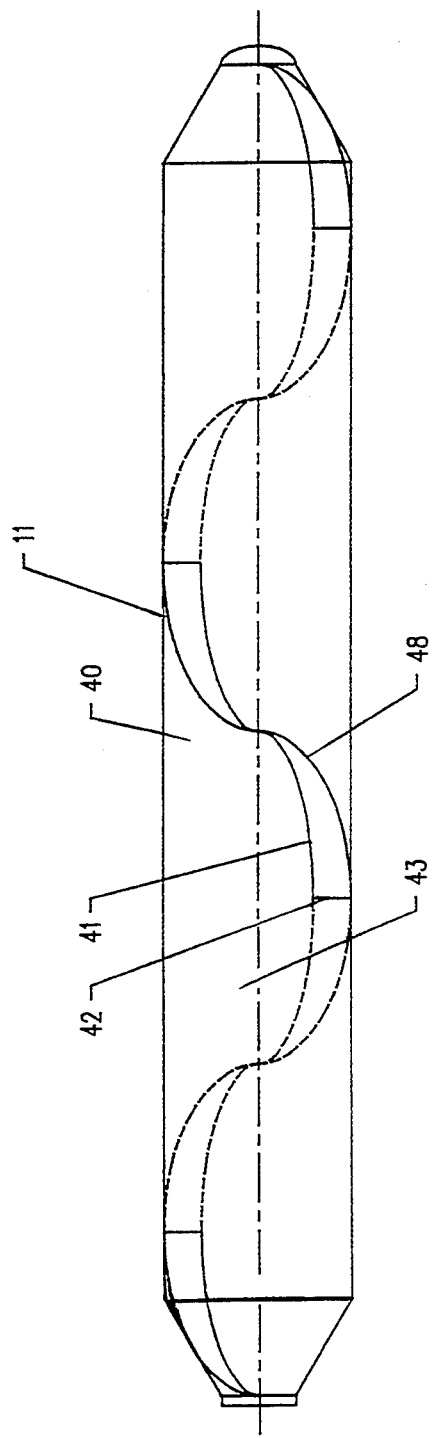
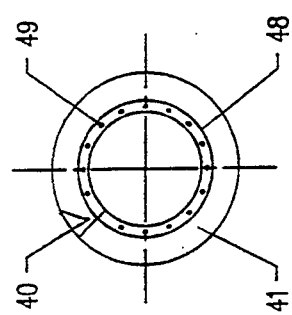
Figure 2
Figure 3

APPARATUS AND METHOD FOR PREPARATION FOR SEPARATION, RECOVERY, AND RECYCLING OF MUNICIPAL SOLID WASTE AND THE LIKE

FIELD OF THE INVENTION

This invention relates to a method and apparatus for recovering valuable materials (glass, plastics, metals, cellulose, etc.) from municipal, agricultural and other waste including solid waste (MSW) and converting paper, cardboard, food waste, etc. to a usable cellulose material and separating it from other recyclable materials.

BACKGROUND OF THE INVENTION

One of the major problems confronting our society today is the generation of wastes. Landfilling had become the method of choice with the prevailing mentality being "Out of Sight—Out of Mind!". The most commonly considered alternatives to landfills are mass incineration of municipal waste and its related activity, the production of refuse derived fuel (RDF). Incineration and refuse derived fuel produce a variety of pollutants that cause respiratory discomfort and disease. These pollutants are caused by incomplete combustion of municipal solid waste and the oxidation of plastics in the presence of metals.

It is known that municipal solid waste contains many materials of value, when recycled. Environmentalist and public officials view the recycling of these materials as the most desirable method of waste disposal; however, present recycling efforts have reduced the volume of MSW by less than ten percent.

In light of the shortcomings, both technically and economically of mass-burn and refuse derived fuel and with an awareness of the wealth of recyclable materials being lost in landfills, a method of easily classifying and separating recyclables is needed.

In my prior U.S. Pat. No. 4,342,830, dated Aug. 3, 1982, steam treatment of MSW is disclosed wherein the sterilized and softened organics are forced through perforations upon sudden release of pressure whereby inorganics and certain synthetics, such as metal cans, glass, plastic containers and the like, are left behind. This method was aimed at the production of ethanol and included the addition of significant quantities of water to the wastes and thus required substantial energy consumption in the form of steam to heat the water/waste slurry, transform it into a pulp and to force the resultant sterile and pulped organics through the perforations in a singular step. The pulped organics were intended primarily for ethanol and animal food production. The plastic recovered which were suitable for recycling were generally less than 2% of the waste by weight and were generally severely contaminated with softened organics and dirt. The inorganic materials such as ferrous and non-ferrous metals were also similarly contaminated, making these products less desirable for recycling. The glass components were both broken and contaminated.

In my prior U.S. Pat. No. 4,540,495, dated Jun. 10, 1985, steam treatment was again disclosed wherein the amount of water added prior to steam treatment was significantly reduced to conserve energy consumed and to limit the residual moisture content of the softened organic fraction to the order of 60%–70% by weight. Further test have proven the stated water added to the final moisture content of the pulp (in my U.S. Pat. No. 4,540,495) is necessary to ethanol production but is not necessary for other uses. For example, it is not essential to have a 60%–70% moisture content in the pulp for effective screening. Tests have proven that effective screening can be accomplished at final moisture content ranges as low as approximately 30%–40%. If desirable, the pulped material can be screened when completely dry.

There was no method disclosed in my U.S. Pat. No. 4,540,495 for controlling final moisture content of the softened organic fraction; therefore, making final separation more difficult and decreasing the desirability of the plastics, and inorganic recyclables. However, further test have proven that lower residual moisture content than that stated facilitates easier separation of the processed waste components. It has also been determined by further testing that efficient heat-mass transfer and efficient mixing are not limited by the 70% ratio of input volume and vessel volume as stated in my U.S. Pat. No. 4,540,495.

Time, moisture content, pH, pressure, temperature and viscosity are all essential variable to be adjusted to determine the final condition of the processed waste. The addition of surfactants, acids, caustic, moisture, heat, vacuum, and varying the length of the mixing period are all steps that may be taken to achieve the desired end result. Actual application of the prior patent parameters revealed that the internal steam pressure requirements in combination with the resultant temperatures and the necessary period of time required to "cook" and sterilize the waste material and soften the organic matter also caused a melting of many of the plastics and significant heat distortion of most other plastics as in the previous U.S. Pat. No. 4,342,830.

Also in my prior U.S. Pat. 4,844,351, primarily, a method for separation, recovery, and recycling of plastics from municipal solid waste was disclosed wherein mixed wastes including various plastic elements were subjected to mechanical agitation and heat distortion. The wastes were introduced into a processing unit having a means for heating and a means for agitating the wastes. By this method, the plastics were recovered as a mixture that may be recycled, but due to lack of control of the variables as mentioned above, the cellulose residuals were less than desirable. As set forth herein, by controlling pH and other variables, the moisture content and heat may be reduced to yield cellulose to customized specifications, yet leave the plastic in a form that is recyclable.

The above noted defects of the prior art are overcome by the method and structure of the present invention which overcomes the deficiencies of the prior inventions as set forth above and provides an efficient process for the treatment of municipal solid waste (MSW). The waste materials are introduced into a pressurized, heated, rotatable pressure vessel and subjected to controlled conditions wherein a fluid is injected into the pressure vessel and the amount of moisture, the pH level, caustic environment, the viscosity of the fluid, the temperature and the pressure is controlled as the waste material is tumbled and mixed to substantially "fluidize" or pulp the organic material thus making it more easily separated from the inorganic materials such as glass, metals, etc.

The moisture inside of the vessel has its pH controlled by the addition of an acid into the vessel. The viscosity of the moisture environment is controlled by the addition of a surfactant into the vessel to control the surface tension of the materials in the vessel. The caustic substances (such as sodium, hydroxide or the like) may be added to control the chemical disintegration of some waste materials in the vessel.

SUMMARY OF THE INVENTION

It is the object of the present invention, therefore, to provide a method and apparatus for the efficient preparation of recyclable materials for separation and recovery and to be able to vary the condition of the final cellulose and other products to meet custom specification.

It is another object of the present invention to provide such method and apparatus which facilitates the separation and recovery of the recyclable materials in a rapid, facile, and inexpensive manner.

In accordance with the objects, the present invention contemplates the provision of a mixing mechanism which mixes the waste materials, while the waste materials are subjected to heat and pressurization, additional moisture (if necessary), pH adjustment, addition of surfactants, and application of vacuum (to control moisture content of the product). The waste materials are introduced into the chamber and with the chamber closed, the waste materials are agitated in the chamber and steam, water (if needed), an acid, a caustic and a surfactant is added either individually or collectively, as desired. The material is agitated for a predetermined time. A vacuum may be applied to the vessel to remove excess moisture. The vessel is then opened and the material is discharged for separation. Final moisture content of the treated waste is controlled within predetermined limits (35% to 45%).

BRIEF DESCRIPTION OF THE DRAWINGS

FIG. 2 is a diagrammatic longitudinal sectional view of the pressure vessel of FIG. 1.

FIG. 3 is a sectional view of the pressure vessel of FIGS. 1 and 2.

DETAILED DESCRIPTION OF THE INVENTION

Figure 1:
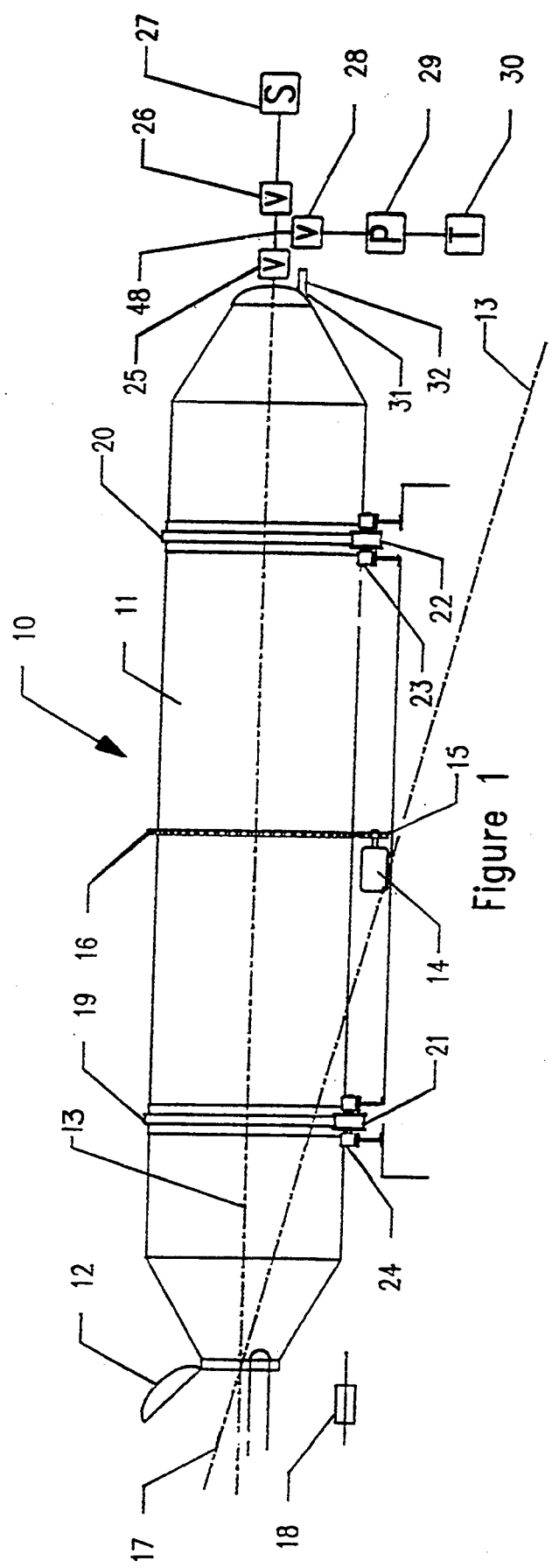
FIG. 1 is an elevational, diagrammatic view of the pressure vessel and feed mechanism therefor according to the principles of my invention.

The pressure vessel 11 (cylindrical, for example) may be rotatably mounted in a set of wheels 19 and 20 secured to the periphery, of the vessel. These wheels 19 and 20 are supported by a set of wheels 21 and 22 which are supported by roller bearings 23 and 24. Also, if desired, the vessel may be inclined at a predetermined angle as illustrated by line axis 13 of FIG. 1.

As seen in FIG. 2, the inner surface 40 of vessel 11 is provided with a mixing member (flighting 41) in the form of spaced blades 42 extending from the internal surface 40 of vessel 11 into chamber 43 thereof. The blades may be baffles supported from the wall of the vessel, a single continuous screw member or a sectional arrangement of blades which extends in a helical configuration substantially along the length of the process vessel 11. The spacing of the baffles or screw member should be sufficient to insure proper mixing of the MSW material.

A steam line (sparger line) 48 is mounted on the inner tip of the blades 42, as shown in FIG. 2, or along the inner wall of the vessel shell, if desired, and is provided with spaced openings 49 (FIG. 3) through which steam is directed into the interior of vessel 11. The sparger line 48 acts as a sparger for distributing steam, acid, caustic substances, water, and surfactants throughout the vessel 11. Line 48 also acts as a collection system for moisture upon application of a vacuum on the vessel 11. The external portion of the sparger line 48 is secured to a rotary coupling or valve (indicated as 25 in FIG. 1) which secures the internal steam line to an external source of steam 27 through a valve 26. Such rotary valves or couplings are well known in the art. When acting as a moisture collecting system for moisture, the steam line 48 is secured to a vacuum pump 29 through a valve 28, which evacuates moisture from the interior of vessel 11, and pumps the moisture to holding tanks 30 for reuse in the process vessel 11, therefore, allowing the control of moisture content of the processed cellulose to vary according to the desired end product.

Once the waste material is introduced into the cylindrical vessel 11 and the closure member 12 is closed, appropriate valves 26 are opened and water, acid, caustic substances, surfactants and steam are directed into the interior of the vessel through the sparger line 48. The process vessel 11 is pressurized to a predetermined pressure and rotated for a predetermined period of time, and the internal baffles mix the waste with the additives, moisture, and heat. This process causes any paper (cellulose) and other organic material to loose its bonding agents and results in pulping, leaving these components of MSW as a fluffy cellulose material.

After a predetermined time period (or the desired viscosity is obtained) of the waste materials being subjected to pressurization, heat and additives (discussed hereinbelow) in vessel 11, the vessel is vented through the sparger line 48 and the valve 28 and a predetermined amount of vacuum may be applied to the vessel 11 by the vacuum pump 29, and this moisture may be pumped to the holding tanks 30 for reuse at a later time. This evacuation process allows control of moisture content of the processed waste. The closure member 12 is then opened and processed material is forced out of the vessel 11 by the rotary action of the baffles 42.

The product is discharged through the closure 12 onto conveyor system 18 (FIGS. 1 and 4) and is conveyed to a rotating trommel 60 (FIG. 4) for further classification. The rotating trommel 60 has two perforated screens of different size (for example ½" and 2") openings to classify the material by size. "Fingers" (flexible rods, approximately 6" long) may be attached to the inner screen in a pattern, extending inward toward the center of the trommel to hold sheet material such as films, plastic, rages, etc. away from the inner screen to improve efficiency. Efficiencies of the trommel would also be improved by applying an internal pressure of approximately 15 psig to the interior on the trommel. This trommel would also be suitable for "MRF" applications. The "inner" screen (2" openings) retains the "large fractions" (over 2") of waste while passing "middle and fine fractions" (smaller than 2") to the outer screen. The "outer" screen (½" openings) retains the "middle fractions" of waste (½" to 2"), while passing the "fine fractions" (less than ½") to a conveyor belt.

The "fine fractions" (less than ½") consist of primarily cellulose and small pieces of broken glass with other small pieces of inorganic materials. These "fine fractions" are conveyed to a stoner 61 which is a vibratory bed with air forced through it (fluidized bed separator) or other means of classification and are separated for further use.

The "middle fractions" consist of primarily small pieces of unpulped paper, bottle caps, rocks, small bits of masonry, etc. The "middle fractions" may be conveyed to the batch hopper 62 to be reprocessed in the process vessel. This reprocessing cycle is interrupted periodically to remove nonprocessable items.

The "large fractions" consists of cans, bottles, plastics and other items larger than 2". The "large fractions" are conveyed to a magnetic separator 63 to remove ferrous metal, an eddy current separator 64 to remove non-ferrous metal, a density separator 65 to remove HDPE plastics, a density separator 66 to remove PET plastics, and a manual picking line 67 to remove items previously missed and rags, large pieces of glass, and other valuables. The order of these items is not important and any separation step can be deferred to the manual picking line or additional separation equipment such as a rag picker can be added.

Valuable recyclables are efficiently recovered by the process and apparatus of the present invention. The resulting organic material is 50% to 65% cellulose and has a value as a fuel for combustion, food for microorganisms, construction material such as wallboard, fabric, etc., compost or bio-chemically converted to gas and liquid fuels such as methane or ethanol.

Apparatus and method of the present invention finds application in landfill mining which is the process of excavating a landfill and uses conventional surface mining technology which includes placing the landfill material on vibratory screens or rotary trommels. The upper (inner) screen has larger openings than the lower (outer) screen, which allows the smaller material such as soil to fall through both screens, while middle size items are retained by the screen with smaller openings. Most materials falling through the larger opening screen and retained by the smaller opening screen are recyclables such as metals, glass, plastics and some organic materials. Materials retained by the larger opening screen typically includes fabrics, building materials, wood, etc. and MSW contained in plastic bags. The recoverable material may be processed by application of the principles of the present invention.

It is to be understood that a vibrating screen assembly similar to that described above in conjunction with the landfill mining procedure may be used to separate the waste components directly out of the process vessel 11 in lieu of the rotary trommel 60, if desired.

Figure 4:
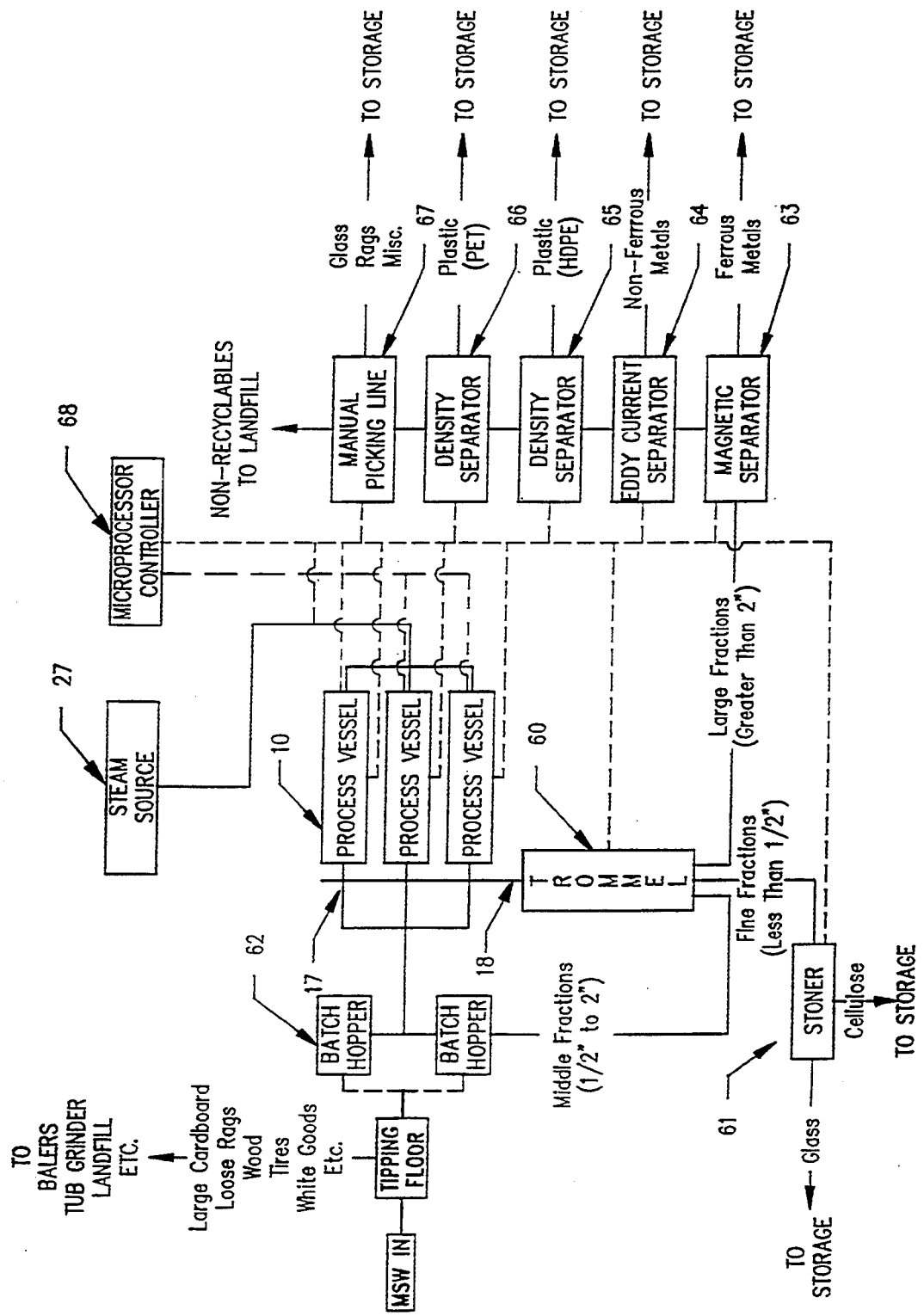
FIG. 4 is a material flow diagram showing the complete process system and all auxiliary equipment.

If desired, the system may be microprocessor controlled as seen in FIG. 4. A microprocessor 68 is connected to actuators to control all valves, motors, and separators. The actuators of the valves, speed control on the motors and safety controls for complete shutdown are all operated by signals from a microprocessor 68 in a manner well known in the art. Actuators of valves are controlled by the microprocessor 68 to open and close at desired times. Motor speed, direction, and operation times are controlled by the microprocessor 68. In FIG. 1, the source of pressure, heat and moisture is shown to be the steam source for the process vessels; however, other sources may be resorted to, if desired. In FIG. 4, specific separation equipment is shown employed for each recyclable or group of recyclables, which are well known in the art; however, specific items may be added or deleted as desired.

In one example of the present invention, the process vessel was 40'-0" long, 8'-0" diameter, and included conical ends with approximately 3'-0" diameter closures. The vessel was designed for 100 psig steam and was similar to the vessel 10 shown in FIG. 2 and FIG. 3. The vessel was rotated at approximately 8 rpm and pressurized to approximately 20 psig with steam, acid, caustic, and surfactants added. Pressure was maintained for approximately 20 minutes. After venting the vessel, the vessel was emptied and the contents observed. Vinegar (5% acidic) was used in one example with good results.

The resulting cellulose material had the appearance of being pulped. It had a moisture content in the order of 40% (in the range of 35%–45%) and was easily separated from inorganics such as glass and metals. Plastics such as HPDE (milk containers with a low melting point) were distorted but easily recovered. Other plastics with higher melting points such as PET showed little distortion. Plastic film materials were distorted into loose balls and easily recoverable. Analysis has shown that pulping occurs (using the above mentioned additives in conjunction with the steam) when the vessel is pressurized in the range of 18–22 psig for a time period in the range of 15–25 minutes.

It is to be understood that the additives may be introduced in the pressure vessel in the manner illustrated in FIG. 1, wherein the additives are shown to be directly injected into the pressure vessel through the sparger line along with or without the steam. To accomplish this, a caustic solution 70, an acid solution 72 and a surfactant solution 74 is connected, respectively, to valves 76, 78 and 80 which control the flow of the additives, either collectively or selectively to the sparger line for injection into vessel 11. A source of pressure (not shown) may be provided to direct the additives into the sparger line or, if desired, the additives may be gravity fed or entrained into the sparger line.

It should be readily apparent, therefore, that the applicant provides a method and apparatus for processing municipal solid waste (including food waste such as fish, etc., agricultural products, etc.) which offers significant improvement over the current state of the art. It should also be apparent that although specific embodiments of my invention are disclosed, various modifications will be apparent to those skilled in the art that is within the spirit and scope of my invention.

I claim:

1. A method for separation of recyclable waste materials from solid waste materials in a pressure vessel having a chamber to receive and pulp said waste materials therein, said method comprising the steps of:

introducing a predetermined quantity of waste materials into a process chamber for processing thereof to pulp said waste materials;

introducing a fluid into said chamber for intermixing with said waste materials for moisturization thereof, said moisture effecting a pulping action on said waste materials;

adding at least one of a plurality of fluid composition altering substances into said fluid for intermixing therewith to change the chemical composition of said fluid for further enhancing the pulping action of said fluid on said waste materials;

heating and pressurizing said chamber and thus said waste materials to a predetermined temperature and pressure for processing the waste materials for a processing period lasting a predetermined period of time;

tumbling said waste materials for mixing thereof during said processing period;

evacuating said chamber for creating a vacuum atmosphere therein for controlling final moisture content of said waste materials in said chamber;

recovering said processed waste material from said chamber for classifying said recovered processed waste material; and separating and recovering recyclable materials from the classified materials.

2. The method of claim 1 including the step of controlling a moisture content of said waste materials during processing thereof so that the final moisture content of said recovered processed waste materials is in a predetermined range.

3. The method of claim 2 wherein said fluid is steam and said heating and pressurization is provided responsive to an introduction of said steam into said process chamber.

4. The method of claim 3 wherein said pressure vessel includes internally mounted vanes and said step of tumbling said waste materials includes rotating said vanes for tumbling and mixing said waste materials during said processing period.

5. The method of claim 4 wherein said vanes are disposed on said vessel and extend into said chamber, and said tumbling is accomplished by rotating said vessel and said vanes in a first direction.

6. The method of claim 5 wherein said vessel includes a common opening serving as an inlet and outlet and the steps of introducing said waste materials into said chamber and recovering said waste materials from said chamber are both accomplished through said common opening and the discharging of said waste materials is accomplished by rotating said vessel in the opposite direction.

7. The method of claim 2 wherein said predetermined final moisture content range is 35% to 45%.

8. The method of claim 1 wherein said plurality of fluid composition altering substances are an acid, a surfactant and a caustic substance.

9. The method of claim 1 wherein said fluid composition altering substance is an acid for controlling the pH of said fluid.

10. The method of claim 1 wherein said fluid composition altering substance is a caustic substance for controlling a caustic action of said fluid on said waste materials.

11. The method of claim 1 wherein said fluid composition altering substance is a surfactant for controlling the viscosity and surface tension of said fluid on said waste materials.

12. The method of claim 1 including the steps of introducing said waste materials into an opening of said pressure vessel and rotating said pressure vessel in a first direction for said tumbling and mixing of said waste materials during said processing period and rotating said pressure vessel in a reverse direction for discharging said processed waste materials through said opening.

* * * * *